United States Patent [19]

Bergeron

[11] 3,974,261
[45] Aug. 10, 1976

[54] PROCESS FOR PURIFICATION OF PHOSPHONITRILIC CHLORIDE POLYMERS

[75] Inventor: Charles R. Bergeron, Baton Rouge, La.

[73] Assignee: Ethyl Corporation, Richmond, Va.

[22] Filed: Nov. 6, 1974

[21] Appl. No.: 521,273

[52] U.S. Cl. .................................................. 423/300
[51] Int. Cl.² ......................................... C01B 25/10
[58] Field of Search .................................... 423/300

[56] References Cited
UNITED STATES PATENTS

| | | | |
|---|---|---|---|
| 3,372,005 | 3/1968 | Jaszka et al. | 423/300 |
| 3,378,353 | 4/1968 | Hands | 423/300 |
| 3,379,510 | 4/1968 | Jaszka | 423/300 |
| 3,677,720 | 7/1972 | Maund et al. | 423/300 |
| 3,694,171 | 9/1972 | Dreifas | 423/300 |

FOREIGN PATENTS OR APPLICATIONS

| | | | |
|---|---|---|---|
| 1,016,642 | 1/1966 | United Kingdom | 423/300 |

*Primary Examiner*—Oscar R. Vertiz
*Assistant Examiner*—Gregory A. Heller
*Attorney, Agent, or Firm*—Donald L. Johnson; John F. Sieberth; James M. Pelton

[57] ABSTRACT

A method for the selective purification of phosphonitrilic chloride polymer mixtures to obtain substantially pure cyclic trimeric and tetrameric phosphonitrilic chloride polymers by distillaton under reduced pressure with inert solvent passed through the molten phosphonitrilic chloride mixture, optionally with prior solvent extraction and/or subsequent recrystallization from solvent.

10 Claims, No Drawings

PROCESS FOR PURIFICATION OF PHOSPHONITRILIC CHLORIDE POLYMERS

BACKGROUND OF THE INVENTION

This invention relates to the purification of phosphonitrilic chloride polymer to obtain substantially cyclic trimeric and tetrameric phosphonitrilic chloride polymers. The preparation of phosphonitrilic chloride polymers is well known in the art. However, certain preferred phosphonitrilic chloride polymers, particularly the cyclic trimer and tetramer, have recently become important for uses in high temperature functional fluids, flame retardant additives, polymers and as intermediates for such uses. Because the prior art processes for producing phosphonitrilic chloride polymers are not specific to these cyclic trimer and tetramer species, there is a need to separate the cyclic trimer and tetramer from mixtures with other higher cyclic and linear phosphonitrilic chloride polymers.

Purification processes known in the prior art include fractional distillation, crystallization and solvent extraction; for example, U.S. Pat. No. 2,788,286, Teja et al., teach the fractional distillation of cyclic trimer and cyclic heptamer from mixed phosphonitrilic chloride polymers at 12 millimeters of mercury and 135°C after preparation of a phosphonitrilic chloride polymer mixture by reacting ammonium chloride and phosphorus pentachloride in tetrachloroethane and quinoline at 145°C, evolving HCl and then distilling off the solvent. In another process for producing phosphonitrilic chloride mixtures, U.S. Pat. No. 3,367,750, to Jaszka et al., teaches producing phosphonitrilic chloride polymers by reacting ammonia and chlorine in an inert solvent to form finely divided ammonium chloride, introducing phosphorus pentachloride into the dispersion and reacting to form phosphonitrilic chloride polymer. In the Jaszka et al. U.S. Pat. No. 3,367,750 process, the purification is carried out by filtering the reaction product, distilling the filtrate to remove monochlorobenzene solvent and washing the crude phosphonitrilic chloride with petroleum ether to extract cyclic polymers and crystallizing the cyclic phosphonitrilic chloride from the petroleum ether. Further, Jaszka et al. in U.S. Pat. No. 3,372,005 teach purifying crude phosphonitrilic chloride polymers at less than 170°C by passing an inert gas through molten crude phosphonitrilic chloride polymer to obtain a polymer laden inert gas. The phosphonitrilic chloride polymer laden inert gas is then contacted with solvent to separate the distilled phosphonitrilic chloride polymer from the inert gas and then the solvent is vaporized from the solution to produce trimeric and tetrameric cyclic phosphonitrilic chloride polymer crystals. In still another process, Jaszka et al. in U.S. Pat. No. 3,379,510 teach a method for separating cyclic phosphonitrilic chloride trimer and tetramer from a liquid mxture of phosphonitrilic chloride polymers and solvent by forming a moving agitated film on a wiped film evaporator wall, heating the film to vaporize the trimer, tetramer and solvent and separating the vapor and liquid phases containing higher molecular weight polymers. The vapor phase is then cooled and the cyclic trimeric and tetrameric phosphonitrilic chloride polymers are separated from the solvent. In a variation on the Jaszka et al. U.S. Pat. No. 3,372,005 patent, Maund et al. in U.S. Pat. No. 3,677,720 teach a process for selectively purifying mixtures of phosphonitrilic chloride polymers by heating a mixture of process solvent and the polymer, flashing off solvent which is superheated and then countercurrent contacting the superheated inert solvent vapor with polymer so as to selectively vaporize cyclic trimer. The solvent vapor phase laden with trimer and some tetramer is separated from the molten polymer residue, condensed and the trimer and tetramer recovered from the solvent solution. In another type of process, U.S. Pat. No. 3,694,171 to Dreifus teaches contacting a solution of phosphonitrilic chloride in monochlorobenzene solvent with aqueous caustic, separating the resultant aqueous phase from the polymer solution, and then separating the resultant solution of cyclic trimer and tetramer from the aqueous phase.

In each of the above identified prior art processes, material handling is difficult or process equipment requirements are large and there is a need for a simpler process which has the advantage of omitting steps of the prior art processes and simplifying equipment requirements, thus lowering capital investment and improving process economics. The process of the present invention has these advantages while, nevertheless, producing product of the quality of the prior art or better.

SUMMARY OF THE INVENTION

There is provided, according to this invention, a process for purifying crude phosphonitrilic chloride polymers by heating molten phosphonitrilic chloride polymer while passing an inert solvent vapor through the molten mixture at a sufficient rate to obtain cyclic trimer and tetramer in the vapor, then condensing the mixture of solvent vapor and cyclic trimer and tetramer and separating the cyclic trimeric and tetrameric phosphonitrilic chloride from the condensed solvent.

Typically, the molten phosphonitrilic chloride polymer is at a temperature up to about 190°C and the inert solvent is different from the processing solvent in which the phosphonitrilic chloride mixture is prepared. Preferably, the inert solvent is a normally gaseous hydrocarbon at the temperature of the molten phosphonitrilic chloride mixture, and most preferably is a saturated aliphatic hydrocarbon having from 6 to 8 carbon atoms.

DESCRIPTION OF PREFERRED EMBODIMENTS

According to the process of the present invention, the starting material is a mixture of phosphonitrilic chloride polymer which may be produced according to known processes, such as those cited in the Background of the Invention. Accordingly, the crude phosphonitrilic chloride polymer mixture contains a substantial amount of phosphonitrilic chloride other than the cyclic trimer and tetramer. It should be noted that the phosphonitrilic nomenclature will be used in this specification, but that these polymer mixtures could as well be described by the phosphazene nomenclature as mixtures of cyclic and linear chlorophosphazenes from which it is desired to separate the cyclic hexachlorotriphosphazene and octachlorotetraphosphazene.

Typical proportions expressed as percentages by weight of the crude phosphonitrilic chloride polymers obtained by prior processes are 75–85 percent of cyclic polymer and 15–25 percent of linear polymer. Furthermore, the proportions of individual cyclic polymers found in the crude mixture of cyclic and linear polymers are approximately 30–60 percent of the trimer, 10–30 percent of the tetramer, and 30–40 percent of the higher cyclic polymers in which the percentages of various polymers are expressed as percentages by weight. The proportions of cyclic and linear polymers are not critical and may be varied to some extent. Variation in the amounts of phophorus pentachloride and ammonium chloride used, the temperature and amount of solvent employed and the particle size of ammonium chloride will affect the composition of the crude polymer mixture. Ideally, a process producing only the cyclic trimer or tetramer or a mixture thereof from the starting materials without the necessity for subsequent upgrading or purification would be preferable. However, practical processes for doing so are not known as evidenced by the prior art on purification of crude phosphonitrilic chloride mixtures.

A praticularly advantageous process for preparation of crude mixtures of phosphonitrilic chloride polymers from phosphorus pentachloride and ammonia can be carried out in the presence of hydrogen chloride under a pressure from 10–40 psig by introducing ammonia into a slurry of phosphorus pentachloride in an inert solvent in which the ammonia is introduced at the beginning of the reaction into the slurry at a rate of not less than 0.13 liters per minute per mole of phosphorus pentachloride until an amount corresponding to about one-tenth to about one-half of the total ammonia has been added. The slight hydrogen chloride pressure is used to facilitate formation of ammonium chloride in situ. Such a process is more particularly disclosed in U.S. Pat. No. 3,780,162 to Bergeron, which is incorporated herein by reference as if fully set forth.

It should be noted that the particular method for establishing a crude mixture of phosphonitrilic chloride polymers is not critical since the method for purification only requires a substantial amount of cyclic phosphonitrilic chloride polymers from which the cyclic trimeric and tetrameric phosphonitrilic chloride can be separated. For convenient illustration, the starting phosphonitrilic chloride polymer mixture can be referred to by the general formula $(PNCl_2)_x$

in which $x$ is a whole number of at least 3, and preferably from 3 to about 8. The $(PNCl_2)_x$ mixture generally contains mixtures of cyclic and linear polymers as produced in the prior art processes and such mixtures are useful, convenient and economical starting materials for the process of this invention.

The process is carried out with the starting phosphonitrilic chloride polymer mixture in the molten state. Generally, such polymers are in the molten or liquid state from the conditions of the reaction which produces such polymers and can be used in their fluid or liquid form in the present invention directly from the process for their production. If, in some cases, the polymer mixture has been allowed to cool and solidify, it is only necessary to heat the polymer mixture to a temperature sufficient to melt the polymer. However, the temperature of the molten phosphonitrilic chloride polymer mixture should not be so high as to degrade the polymers. Preferably, the temperature should be less than about 200°C and preferably from molten state up to about 190°C. Various individual phosphonitrilic chloride polymers melt at different temperatures ranging from about 57°–58°C for cyclic octamer $(PNCl_2)_8$ to 123.5°C for cyclic tetrameric phosphonitrilic chloride $(PNCl_2)_4$. Cyclic trimeric phosphonitrilic chloride polymer $(PNCl_2)_3$ melts at 114°C. Therefore, the temperature of the molten mixture should be at least about 120°C. After the polymer mixture becomes molten, the temperature is gradually increased during the distillation. However, as indicated above, the temperature should not be increased above the temperature at which substantial degradation of the polymer mixture takes place, say about 200°C, and preferably not more than up to about 190°C. Therefore, it is preferred to conduct the process of this invention by distilling the crude polymer mixture at from about 120° to about 190°C.

According to the process of the present invention an inert solvent is passed through the molten phosphonitrilic chloride polymer at a rate sufficient to obtain solvent vapor containing the cyclic trimeric and tetrameric phosphonitrilic chloride polymers. The inert solvent is preferably different from the processing solvent. As indicated above, prior art processes have used inert gases, such as helium argon, air, methane, nitrogen and carbon dioxide and mixtures of these (see Jaszka et al. U.S. Pat. No. 3,372,005) or processing solvent, such as monochlorobenzene or other chlorinated hydrocarbon solvents or phosphorus oxychloride. Other prior art chlorinated hydrocarbon solvents include trichlorobenzenes, orthodichlorobenzenes, symmetrical tetrachloroethane and tetrachloroethylene, as well as benzoyl chloride, chloroform and carbon tetrachloride to remove cyclic trimer and tetramer from phosphonitrilic chloride polymer mixtures. However, it has been found that an inert hydrocarbon solvent which is normally gaseous at the temperatures of the molten phosphonitrilic chloride polymer mixture and the pressure of the present process can be advantageously employed in the process of this invention. For example, if process solvent such as monochlorobenzene were used for purification of the phosphonitrilic chloride polymer mixture with the optional pretreatment to remove linear species, the monochlorobenzene must be removed, the cyclics extracted out with a suitable solvent, such as an inert hydrocarbon solvent and separated from the linear species and then the cyclics separated from the pretreating solvent before again dissolving the cyclic phosphonitrilic chloride polymer mixture with monochlorobenzene to continue purification by distillation. According to the present process, after the optional pretreatment and separation from unextracted linears, the cyclic phosphonitrilic chloride polymers are ready for distillation resulting in a simpler and more efficient process. Also, because of the different solubility characteristics, if the optional pretreatment is not employed any linear species reporting in the distillate are readily observable as a haze in an inert aliphatic hydrocarbon solvent, but not in process solvents such as monochlorobenzene. Typically, the inert hydrocarbon solvent is preferably an aliphatic hydrocarbon and most preferably a saturated aliphatic hydrocarbon solvent. More preferred saturated aliphatic hydrocarbons which may be used in this invention are those boiling within the range of 60°–130°C. Most preferably, the saturated aliphatic hydrocarbon has from about 6 to about 8 carbon atoms. Such hydrocarbons include hexane, heptane, octane, their various isomeric forms or mixtures thereof. Although n-octane boils at 125°–126°C and the minimum temperature described above for the molten phosphonitrilic chloride polymer is 120°C, in practice the process is preferably carried out at less than atmospheric pressures and, accordingly, under the conditions of the process, octane could be advantageously employed.

It should be recognized that for conducting the present process at or near atmospheric pressure, one of the lower boiling solvents is useful when temperatures near the minimum are employed. The inert solvent can be introduced to the phosphonitrilic chloride mixture in either the gaseous or liquid state. If the gaseous state is desired vaporizing means are required to form the gas from the solvent which are normally obtained in large quantities as a liquid. If the liquid state is used, additional heating is required in the vessel containing the molten phosphonitrilic chloride polymer mixture to carry the additional heat load. It is preferred to introduce the inert solvent as a liquid because of more efficient contacting being obtained with the polymer and the formation of gas bubbles causes good agitation.

The inert solvent is passed through the molten phosphonitrilic chloride polymer sufficiently to obtain the solvent vapor containing cyclic trimeric and tetrameric phosphonitrilic chloride polymers from the polymer mixture. Generally, the rate of solvent passing through the molten phosphonitrilic chloride polymer mixture is not critical and can be chosen with regard to practical considerations, economy of operation and reasonable cycle time. The flow rate of inert solvent should be such that higher cyclic polymers and any linear polymers remaining in the phosphonitrilic chloride polymer mixture are not carried over with the cyclic trimer and tetramer by physical entrainment of liquid. Preferably, practical rates can be based on the amount of phosphonitrilic chloride material, and typical rates could range from 0.003 to about 0.25 gram mole of solvent per minute per gram mole of phosphonitrilic chloride polymer initially present. Preferably, the rate of inert solvent flow is from about 0.02 to about 0.125 gram moles of inert solvent per minute per gram mole of phosphonitrilic chloride.

The process of this invention is preferably carried out at pressures lower than atmospheric in order to employ reasonable and practical temperatures, solvent flow rates and to use equipment which does not require a high temperature capability. Although atmospheric pressure and pressures greater than atmospheric pressure can be employed, it is preferred to use subatmospheric pressures in the process of the present invention. By doing so, lower temperatures can be employed which decreases the possibility of degradation of the starting phosphonitrilic chloride polymers. Preferably, pressures for the operation of the present process of from about 40 to 70 torr can be employed. Although pressures as low as 25 torr or less can be used. Certainly, higher pressures can be employed if higher temperatures are also employed.

The process of this invention is carried out until a substantial portion of the trimer and tetramer are removed from the starting polymer. In general, distillation rates decrease and the amount of trimer and tetramer carried over by the solvent decreases with time. Thus, the time of distillation is not critical but depends on such factors as the solvent flow rate, temperature, pressure, desired yield and formation of materials in the distillate which might adversely affect the process. Further, the scale at which the process is carried out will also affect the time required for distillation. Theoretically, as soon as the distillate is formed and condensed the process has effected some purification, but it would be entirely impractical to conduct the process for recovery of small amounts of purified cyclic trimer and tetramer. Preferably, the process is carried out for times of about 1 to several hours, but such times are illustrative and should not be considered as critical to the process.

The solvent vapor containing cyclic trimeric and tetrameric phosphonitrilic chloride polymers is condensed forming a liquid mixture of solvent and trimeric and tetrameric cyclic phosphonitrilic chloride polymers. The trimer and tetramer can then be easily separated from the condensed solvent by known techniques, for example, by fractional crystallization or evaporation of the solvent.

In many instances, it is preferable to conduct a pretreatment of the phosphonitrilic chloride polymer mixture to eliminate linear phosphonitrilic chloride polymers. These linear species form tars melting at temperatures higher than the desired trimer and tetramer making clean-up of process equipment difficult, reducing heat transfer and trapping desirable polymer. Further, according to Maund, U.S. Pat. No. 3,677,720, at temperatures employed in the process, these linear materials catalyze the formation of higher polymers, thus reducing yield of desired cyclic trimer and tetramer polymer products. Accordingly, it is preferable in many instances to remove these reactive linear species by suitable pretreatment prior to conducting the purification process of the present invention. Removal of linear polymers can be carried out as known in the prior art, for example, by extracting with petroleum ether. In general, it is only necessary to treat the crude phosphonitrilic polymer mixture with a material which is a solvent for the cyclic polymer species and which is a non-solvent for the linear species. Such a material is generally different from process solvents which are solvents for both cyclic and linear polymer species. Typical solvents for the cyclic species are paraffinic hydrocarbons such as hexane, heptane, octane and the like, petroleum ether which is a petroleum fraction boiling in the range from about 40 to about 60°C, and the like. Preferably, the pretreatment solvent is the same inert solvent used in the purification or distillation process so that an additional solvent separation step is not required. Accordingly, when combined with the purification process of the present invention, the pretreatment of crude phosphonitrilic chloride polymer mixtures with petroleum ether, or more preferably the inert solvent, to eliminate linear phosphonitrilic chloride polymers from the mixture is a preferred embodiment of the invention.

The process of the present invention can be more easily understood by reference to the following examples which are illustrative and not limiting of the invention. In general, the procedure followed by the process of the present invention involves charging a solid mixture of crude phosphonitrilic chloride polymers to a suitable reaction vessel equipped with heating means, agitator, thermometer, solvent inlet means and connecting means to a condenser suitable for condensing the distillate which is a mixture of the inert solvent, trimer and tetramer. The heating means is activated in the distillation vessel and the crude phosphonitrilic chloride polymer melted. Of course, if the purification procedure directly follows the preparation of phosphonitrilic chloride polymer, this heating step may not be necessary since the evaporation of process solvent would leave a crude mixture of molten phosphonitrilic chloride in an evaporation vessel. When the crude polymer mixture becomes molten, the agitator and solvent flow are started. In general, the solvent can be liquid providing good contact with the molten polymer and will vaporize in the distillation vessel at the temperature of the molten polymer providing good agitation. However, it could as easily be vaporized prior to entering the distillation vessel. To aid in the distillation, reduced pressure can be advantageously employed. As the heating of molten polymer mixture continues at reduced pressure and with the solvent vapor passing through the molten mixture under agitation, the solvent vapor comes off overhead and carries cyclic phosphonitrilic chloride trimer and tetramer with it to the condenser. The heating is continued until a substantial portion of trimer and tetramer are distilled off. Upon cooling the distillate in the condenser, the trimer and tetramer crystallizes from the solvent and can be filtered and/or recrystallized to obtain substantially pure trimeric and tetrameric phosphonitrilic chloride polymers. Alternatively, the solvent can be evaporated leaving solid cyclic trimer and tetramer product.

In a preferred procedure, the crude polymeric phosphonitrilic chloride mixture can first be treated with petroleum ether or other paraffinic hydrocarbon solvent such as hexane, heptane or the like in which the cyclic phosphonitrilic chloride polymers are soluble and thus aid in separating the undesirable linear species from the cyclic trimer and tetramer.

EXAMPLE I

A crude mixture of solid phosphonitrilic chloride polymers was contacted with hexane to dissolve cyclics and remove linear species from the mixture. The washed polymer mixture contained 49.5 wt % trimer, 18.3 wt % tetramer, 8.3 wt % pentamer, 3.0 wt % hexamer, 3.2 wt % unknowns and 4.4 wt % monochlorobenzene. The remainder by difference was 13.3 wt % linear species removed by separating in hexane pretreatment. Then, 532 grams of the solvent-washed phosphonitrilic chloride polymer mixture was added to a 500-ml distillation vessel equipped with heating means, agitator, thermometer, solvent inlet tube and connected through appropriate heated tubing to a condensing receiver. The receiver flask which was situated in an ice bath was connected through a dry-ice trap to a vacuum pump. Then, 1300 ml of normal heptane was placed in a 2-liter solvent reservoir connected to a nitrogen pressurization source above the liquid surface of the solvent. The solvent inlet tube from the distillation vessel was connected to the solvent reservoir with the end of the tube below the liquid level of the solvent. In the solvent inlet tube was placed a flow meter and a regulating needle valve. The heater on the distillation vessel was turned on to melt the phosphonitrilic chloride polymer mixture. When the temperature in the distillation vessel reached 175°C, the solvent inlet valve was opened and the solvent began flowing through the distillation vessel. Pressure was regulated at 60 torr by the vacuum pump and stirring was set at medium speed. The flow of heptane was started slowly and increased gradually during the first 45 minutes of distallation. The average flow rate was 6.3 ml/min. The distillation temperature decreased slightly after turning on the heptane feed to 164°C and then rose slowly over the next hour and 10 minutes to 187° C. When the temperature reached 190°C, all of the heat was turned off and the heptane flow was stopped. The distillation residue was 140 grams and the amount of distillate in the receiver was 794 grams. This was divided into two portions. The first portion was stripped of solvent to dryness on a rotary dryer under high vacuum at 60°–70°C and the product weighed 175 grams. This product analyzed 97.7 percent trimer and 3.7 percent tetramer, representing a yield of 68 percent based on one-half of the starting amount of phosphonitrilic chloride and a 93.3 percent yield of trimer on the same basis. The second portion was allowed to crystallize at room temperature, filtered, washed with heptane, rotary dried to remove solvent, flushed with nitrogen, rotary dried again and weighed 104 grams. This represents a yield of 40.5% based on one-half the amount of starting material and 56.1% yield of trimer on the same basis. The recrystallized product from the second portion analyzed 100.9 wt % trimer and no tetramer, pentamer or hexamer by vapor phase chromatographic analysis. The residue from the distillation pot was analyzed to contain 12.8% trimer, 28.3% tetramer, 16.7% pentamer and 7.1% hexamer.

By a procedure similar to Example 1, several additional runs were made. The results are given in the following examples.

EXAMPLE II

The procedure is similar to that used in Example I. The distillation vessel was charged with 525 grams of a mixture of phosphonitrilic chloride having the following analysis:

| | |
|---|---|
| Trimer | 62.8 wt % |
| Tetramer | 11.1 wt % |
| Pentamer | 7.2 wt % |
| Hexamer | 2.4 wt % |
| Heptamer | 0.6 wt % |
| Linears (by difference) | 15.9 wt % |

However, in this case the mixture of phosphonitrilic chloride polymers was not washed with hexane to eliminate linear species from the mixture. To the solvent reservoir was charged 1.3 liters of heptane. After melting the crude phosphonitrilic chloride polymer, the temperature of the material in the distillation vessel was increased from 165°–195°C over a period of 1 hour and 80 minutes. Likewise, during this distillation, the heptane temperature was increased from 78°–100°C and the heptane flow rate was started and gradually increased over the first 35 minutes and then maintained at a fixed rate. The average flow rate of heptane was 7.5 ml/min. The distillation was carried out under pressure of 50 torr. The distillate was divided into two parts. In the first part, about one-third of the heptane was stripped off and the remainder was allowed to crystallize at room temperature. The solids were filtered, washed in heptane and the solvent evaporated to produce a phosphonitrilic chloride mixture weighing 110 g. Analysis showed this material to be 99.5% cyclic trimer. This represents an overall yield of 41.9% based on one-half of the starting phosphonitrilic chloride mixture, and a yield of 66.4% trimer on the same basis.

The second part of the distillate was stripped to dryness under high vacuum about 3–5 mm Hg at 60°–70°C giving 152 g product and analyzed 95.8 wt % cyclic trimer, 4.6 wt % cyclic tetramer. The overall yield for the second portion was 57.9% with 89.4% being trimer, both yields being based on one-half of the starting material. The residue from the distillation vessel weighed 180 g and contained a cyclic phosphonitrilic chloride mixture having 4.8% trimer, 15.6% tetramer, 12.9% pentamer and 6.6% hexamer.

EXAMPLE III

A similar procedure to Example I was followed except that the equipment included a 1-liter distillation vessel and 2-liter heptane reservoir and 2-liter distillate receiver. To the distillation vessel was charged 1,184 g of a phosphonitrilic chloride polymer mixture having the following analyses:

| Trimer | - | 49.5 wt % |
|---|---|---|
| Tetramer | - | 18.3 wt % |
| Pentamer | - | 8.3 wt % |
| Hexamer | - | 3.0 wt % |
| Unknowns | - | 3.2 wt % |
| Monochlorobenzene | - | 4.4 wt % |

The remainder by difference was 13.3 wt % linear species which was eliminated from the crude mixture of solid cyclic phosphonitrilic chloride polymers by washing with hexane as in Example I. The washed phosphonitrilic chloride polymer mixture was heated to 140°C at which time the heptane flow was started. Then, the temperature was increased to 186°C over a period of 130 minutes. The heptane temperature in the reservoir was also increased from room temperature to 80°C. Flow rate of heptane averaged 7.7 ml per minute during the distillation. Distillation was carried out under a pressure of 70 torr. The weight of phosponitrilic chloride remaining in the distillation flask was 303 g. One liter of heptane was used during the distillation. The distillate was filtered hot through a diatomaceous earth, washed with heptane, about 200 ml, and the filtrate weighing 1,647 g was divided into 3 portions. A 229 g portion was rotary-stripped under high vacuum at 60°-70°C to give 114 g of product analyzing 95.7 wt % cyclic trimer and 3.4 wt % cyclic tetramer, representing a yield of 69.2% overall and 95.6% based on trimer, both based on about 14% of the starting phosphonitrilic chloride mixture. A second portion of 378 g of the filtrate was allowed to crystallize at room temperature. It was then cooled in an ice water bath for about 15 minutes, filtered, washed with heptane, and dried in a rotary stripper to give 151 g of solid phosphonitrilic chloride polymer mixture analyzing 99.7 wt % cyclic trimer, representing an overall yield of 55.6% and a trimer yield of 79.4% based on about 23% of the starting phosphonitrilic chloride. A third portion of the filtrate from the distillation, the remainder of the solution, was allowed to crystallize at room temperature. It was then cooled in an ice water bath, filtered, washed with heptane, filtered again and weighed 390 g. To this solid material was then added 500 ml of hot heptane which resulted in a clear solution. The phosponitrilic chloride was allowed to crystallize from the heptane at room temperature and after cooling 15 minutes in an ice water bath was filtered, washed with heptane and rotary-stripped. The product weighed 337 g and was analyzed as 100.7 wt % cyclic trimer. The overal yield on this twice recrystallized material was 45.1% with 64.4% yield of trimer based on about 63% of the starting phosphonitrilic chloride. The residue from the distillation flask analyzed 4.9 wt % cyclic trimer, 33.0 wt % cyclic tetramer, 21.8 wt % cyclic pentamer and 9.2 wt % cyclic hexamer, with 0.3 wt % unknown.

EXAMPLE IV

Following the procedure of Example I and using similar equipment 506 g of phosphonitrilic chloride polymer mixture similar to that used in Example I was heated to melting at about 128°C, the stirrer was activated and heptane, about 1,425 ml, in the heptane reservoir was heated to 53°C. After 10 minutes at 142°C in the distillation vessel the heptane flow was begun and the pressure in the distillation vessel held at 73 torr. The distillation started at this point and continued for 115 minutes with the temperature reaching 166°C at the highest point and the average flow rate of heptane of 6.74 ml/min. The heptane temperature was also increased to 90°C. After this, the heating was discontinued and the flow of heptane stopped. There was 650 ml of heptane left in the reservoir and 195 g of phosphonitrilic chloride polymers remaining in the distillation vessel. The distillate was filtered hot through a diatomaceous earth and the weight of the filtered solution was 900 g. This was divided in half and a 450 g sample was partially stripped, removing 80 g of heptane and then allowed to cool and crystallize. The sample was further cooled in an ice water bath for about 15 minutes, filtered, washed with heptane and stripped to produce 110 g of solid cyclic phosphonitrilic chloride polymers analyzing 99.5 wt % trimer with 0.4 wt % unknown. The recovered yield of the crystallized material in the first portion of the product was 43.5% of which the cyclic trimer yield represented 65.2%, both based on one-half of the starting material. The remaining portion of the distillate solution was stripped to dryness and amounted to 140 g of phosphonitrilic chloride analyzing 97.1 wt % trimer, 2.3 wt % tetramer. The residue analyzed 33.3 wt % of trimer, 32.4 wt % tetramer, 16.6 wt % pentamer and 8.3 wt % heptamer.

EXAMPLE V

Following the procedure of Example I and using a similar crude mixture of phosphonitrilic chloride polymers, 490 g of hexane-treated phosphonitrilic chloride polymers were heated to melt the phosphonitrilic chloride mixture. Then, 1,650 ml of heptane were placed in the reservoir. When the temperature of the phosponitrilic chloride polymer mixture reached 155°C, the heptane flow was started with the temperature of heptane being 60°C and the pressure in the distillation vessel being 45 torr. Heating was increased to 168°C and distillation allowed to continue for 135 minutes. During this time, the heptane temperature was increased from 60°-85°C and the flow rate averaged 6 ml per minute. After 135 minutes, heating was discontinued, the heptane flow stopped and the pressure returned to atmospheric with nitrogen. There remained 136 g of phosponitrilic chloride polymer residue in the distillation flask and 1,020 ml of heptane was left in the reservoir. The distillate was heated to dissolve solids, filtered hot through a diatomaceous earth, forming a clear solution weighing 844 g. Half of the filtrate, 422 g, was rotary-stripped at high vacuum to about two-thirds of the volume and the phosphonitrilic chloride polymer was allowed to crystallize overnight at room temperature. Then the filtrate was cooled in an ice water bath about 30 minutes, filtered, washed with heptane and allowed to crystallize under nitrogen. The solution was then rotary dried under high vacuum at 60°-70°C and 132 g of product phosphonitrilic chloride polymer mixture, analyzing 98.4% trimer, was obtained. The product represented an overall yield of 53.8% and 76.3% yield of trimer, both yields based on one-half of the starting phosphonitrilic chloride. The remainder of the distillate was stripped to dryness under high vacuum on a rotary stripper at 60°–70°C, yielding 160 g of product phosphonitrilic chloride polymer, analyzing 95.9 wt. % trimer and 2.2 wt. % tetramer.

EXAMPLE VI

In equipment similar to Example III, 1,259 g of hexane-extracted phosphonitrilic chloride polymer, similar in analysis to the polymer of Example I was charged to the distillation vessel. Then, 1.5 liters of normal heptane was added to the heptane reservoir. After melting the phosphonitrilic chloride mixture at 135°C, stirring was started and heptane flow at 40°C was started at a rate of 2 ml per minute and the distillation vessel was under pressure of 43 torr. After 70 minutes, a first cut was removed from the distillate receiver during which time the temperature had increased to 168°C in the distillation vessel and the heptane in the reservoir was 90°c. The heating and distillation continued for another 60 minutes during which the temperature was about 170°C and the pressure was 40 torr. There remained 650 ml of heptane in the reservoir and the residue in the distillation flask was 437 g. The average flow rate of heptane for both cuts was 5.85 ml/min.

The first cut was heated to dissolve the solids, forming a clear solution weighing 516 g. One-half of this solution was stripped to about two-thirds volume and allowed to stand and crystallize. Then, it was cooled in an ice water bath for 30 minutes, filtered and washed with heptane, then rotary dried under high vacuum at 60°–70°C, producing 97 g of white crystals, analyzing 99.8 wt % cyclic trimer. The other half of the first cut, weighing 258 g, was stripped to dryness using a rotary stripper at high vacuum and 60°–70°C to obtain 112 g of solid phosphonitrilic chloride polymer mixture. This mixture analyzed 97.8 wt % cyclic trimer, 0.2 wt % cyclic tetramer.

The second cut was heated to dissolve the solids, adding more heptane to form a clear solution weighing 981 g. It too was divided in half and the first half was concentrated to about two-thirds volume by removing solvent, allowed to crystallize and further cooled in an ice water bath for 30 minutes. Filtering, washing with heptane and finally drying on a rotary dryer under high vacuum at 60°–70°C produced white cyrstals weighing 210 g and analyzing 98.5 wt % cyclic trimer. The second half of the second cut was stripped to dryness on a rotary stripper with high vacuum at 60°–70°C. The product weighed 246 g and analyzed 95.2 wt % cyclic trimer, and 3.2 wt % cyclic tetramer.

EXAMPLE VII

Following the procedure of Example I, 523 g of hexane treated crude phosphonitrilic chloride having analysis given in Example I was charged to the distillation flask and one liter of heptane was charged to the reservoir. After heating to melt the phosphonitrilic chloride polymer mixture, heptane flow started at an average rate of 6.2 ml per minute when the temperature in the distillation vessel was 137°C. Temperature in the heptane reservoir was 65°C. Pressure in the distillation vessel was 69 torr. Temperature in the distillation vessel was increased to 180°C over 100 minutes and the temperature in the heptane reservoir increased to 90°C. After 100 minutes, heating was discontinued, the flow of heptane was stopped and the pressure on the system was returned to atmospheric with nitrogen. The residue remaining in the distillation vessel was 153 g and 380 ml of heptane remained in the reservoir. The distillate was heated to dissolve solids forming a clear solution and filtered hot. The weight of the distillate was 901 g.

A 150 g sample of the distillate was removed and stripped to dryness yielding 53 g of product which analyzed as 96.9 wt % cyclic trimer and 1.5 wt % cyclic tetramer. The remainder of the distillate was allowed to crystallize in the heptane, then it was further cooled in an ice water bath for about 30 minutes, filtered, washed with heptane and dried on a rotary stripper under high vacuum at 60°–70°C producing 183 g of phosphonitrilic chloride polymer crystals, analyzing 99.4 wt % cyclic trimer.

EXAMPLE VIII

The apparatus and procedure for this example is similar to Example III except that above the distillation vessel an entrainment separater having a packed bed of glass raschig rings and glass spirals was employed. Crude phosphonitrilic polymer, analyzing 56.8 wt % cyclic trimer, 14.9 wt % cyclic tetramer, 7.6 wt % cyclic pentamer, 3.9 wt % cyclic hexamer, 2.7 wt % cyclic heptamer, 0.85 wt % unknowns, 1.32 wt % monochlorobenzene and 11.93 wt % linears (be difference), was extracted with heptane to eliminate the linears and 1,084 g of the heptane extracted phosphonitrilic chloride polymer was charged to the distillation vessel. Then, 1.6 liters of heptane were charged to the heptane reservoir and the heptane was heated to 50°C. After heating the polymer to 130°C in the distillation vessel with the system under pressure of 55 torr, the heptane flow was started. Heating continued with distillation for 115 minutes during which the temperature in the distillation vessel was increased to 178°C. The heptane temperature in the reservoir was increased to 94°C and the flow rate averaged 8.25 ml/min during distillation. Pressure in the system was decreased to about 45 torr during the heating period. After the indicated time, the heating was discontinued and flow of heptane turned off. The distillation vessel contained 344 g of the crude phosphonitrilic chloride mixture residue and 650 ml of heptane was left in the reservoir.

The distillate in the receiver was heated to dissolve solids forming a clear solution with a slight trace of solids. The distillate was filtered, washed with about 300 ml of hot heptane and filtered again to give 1,443 g of solution. About 493 g was removed and stripped to dryness giving 238 g of product which analyzed 98.8 wt % cyclic trimer and 2.3 wt % cyclic tetramer and which represents an overall yield of 64.4% and 100% of trimer, both based on the proportion of starting material that the 493 g of distillate for this sample bears to the total distillate produced, or about 34.1% of the starting phosphonitrilic chloride mixture.

The remainder of the distillate was allowed to crystallize overnight at room temperature. After about 1/2 hour further cooling in an ice water bath, the crystallized phosphonitrilic chloride polymer was filtered, washed with heptane and rotary dried under high vacuum at 60°–70°C, producing 365 g of product, analyzing 98.4 wt % cyclic trimer and 0.9 wt % cyclic tetramer, representing 55.6% yield overall and 87.4% yield of trimer based on about 65.9% of the starting phosphonitrilic chloride. The distillation residue, after removing solvent, analyzed 3.4 wt % cyclic trimer, 30.3 wt % cyclic tetramer, 18.3 wt % cyclic pentamer and 9.1 wt % cyclic hexamer.

EXAMPLE IX

In a procedure similar to Example I, 1,290 g of crude phosphonitrilic chloride polymer mixture without prior hydrocarbon extraction having an analysis similar to that of the crude mixture of Example VIII was charged to the distillation vessel and 1.8 liters of heptane was charged to the heptane reservoir. The distillation was carried out to remove two fractions from the crude phosphonitrilic chloride mixture. The first fraction was distilled over a period of 160 minutes after heating to a temperature of 140°C at 55 torr, using heptane at a temperature of 24°C. The temperature in the distillation vessel was increased to 182°C during distillation and the temperature of heptane was increased to 90°C. The flow rate averaged 4.8 ml/min and the pressure decreased to 43 torr during distillation. After the indicated time, heating was discontinued and the flow of heptane was stopped. The system returned to atmospheric pressure with nitrogen and 500 ml of heptane was added to the reservoir.

The second fraction was obtained by distilling at 152°C, with heptane at a temperature of 52°C, a heptane flow rate averaging 4.8 ml/min and a pressure of 21 torr, for an additional 105 minutes during which time the temperature was increased to 208°C, the heptane temperature was increased to about 85°C and the pressure was decreased to 27 torr. After 105 minutes of distillation, the heat was turned off, flow of heptane was turned off and the system returned to atmospheric pressure with nitrogen. A thick residue remained in the distillation vessel. The volume of heptane left in the reservoir was 520 ml, the weight of the residue was 450 g in he distillation vessel.

The first fraction, weighing 1,348, was heated to dissolve solids. A 460 g sample was removed and 600 ml of heptane was added to dissolve all of the phosphonitrilic chloride crystals at room temperature. The solution was poured through a 1¼ inch column with a packed bed height of 6½ inches using 50 g of silica gel ("SilicAr" silica gel 100 mesh from Mallencrkrodt Chemical). The solution flowed rapidly, forming a dark band near the top of the packing. After stripping the heptane, the white crystals obtained weighed 225.2 g and analyzed 96.4 wt % cyclic trimer, 2.8 wt % cyclic tetramer. The remaining portion of Fraction 1, weighing 888 g, was heated to dissolve the solids, filtered hot two times through a diatomaceous earth and washed with hot heptane, about 150–200 ml. The weight of the filtered solution was 1,072 g. It was divided in half and allowed to stand for over 2 days. One-half of the filtered solution was set in the refrigerator to crystallize any remaining phosphonitrilic chloride materials. The solids were filtered after two hours in the refrigerator, washed with cold heptane and rotary dried under high vacuum at 60°–70°C. The phosphonitrilic chloride polymer product weighed 161 g and analyzed as 99.5 wt % cyclic trimer. The other half of the filtered solution in a cork stoppered vessel had picked up some color. Therefore, it was heated to dissolve solids, then filtered again through silica gel as above resulting in a clear solution, rotary stripped to dryness and weighed 216 g. The product analyzed 97.3 wt % cyclic trimer, 3.8 wt % cyclic tetramer.

Fraction 2 from the distillation was heated to dissolve solids, filtered hot through a diatomaceous earth, forming a very slightly hazy solution weighing 655 g. It was divided in half and each half filtered by gravity into a flask for stripping. The first portion was partially stripped of heptane, 75 g removed, and the remainder was set in the refrigerator to crystallize. After crystallization, the sample was filtered, washed with cold heptane and rotary dried to produce 20 g of polymer material analyzing 100.5 wt % cyclic tetramer. The second half of Fraction 2 was stripped to dryness with a rotary stripper using high vacuum at 60°–70°C. The product weighed 35 g and analyzed 10.5 wt % cyclic trimer, 84.5 wt % cyclic tetramer and 2.5 wt % cyclic pentamer.

What is claimed is:

1. A process for purifying crude phosphonitrilic chloride polymers to obtain trimeric and tetrameric cyclic phosphonitrilic chloride polymers comprising passing a solvent vapor which is a saturated aliphatic hydrocarbon having from about 6 to about 8 carbon atoms through molten phosphonitrilic chloride polymer at a rate of from about 0.003 to about 0.25 gram-mole per minute per gram-mole of phosphonitrilic chloride polymer to obtain said solvent vapor containing said trimeric and tetrameric phosphonitrilic chloride polymers, said molten phosphonitrilic chloride polymer being at a temperature up to about 190°, condensing the resultant vapor stream containing said solvent and said trimeric and tetrameric cyclic phosphonitrilic chloride polymers, and separating said trimeric and tetrameric cyclic phosphonitrilic chloride polymers from the condensed solvent.

2. The process of claim 1 wherein said solvent is a saturated aliphatic hydrocarbon having a boiling point in the range of 60° to about 130°C at atmospheric pressure.

3. The process of claim 1 wherein said solvent is heptane.

4. The process of claim 1 wherein said molten phosphonitrilic chloride polymer is at a temperature of at least 120°C.

5. The process of claim 1 in which sais trimeric and tetrameric cyclic phosphonitrilic chloride is separated from the condensed solvent by crystallization from said solvent.

6. The process of claim 1 further characterized in that said solvent is a saturated aliphatic hydrocarbon having from 6 to 8 carbon atoms and said solvent vapor is passed through said molten phosphonitrilic chloride polymer at a rate of from about 0.02 to about 0.125 gram-moles per minute per gram-mole of phosphonitrilic chloride polymer.

7. The process of claim 1 further characterized in that said solvent is heptane, said solvent vapor is passed through said molten phosphonitrilic chloride at a rate of from about 0.02 to about 0.125 gram-mole per minute per gram-mole phosphonitrilic chloride polymer.

8. The process of claim 1 wherein said solvent vapor is a saturated aliphatic hydrocarbon having from 6 to 8 carbon atoms and said molten phosphonitrilic chloride is at a temperature of at least 120°C.

9. The process of claim 1 further characterized in that said solvent is heptane, said molten phosphonitrilic chloride polymer is at a temperature of at least 120°C and said solvent vapor is passed through said molten phosphonitrilic chloride polymer at a rate of from about 0.02 to about 0.125 gram-mole per minute per gram-mole of said phosphonitrilic chloride polymer.

10. The process of claim 1 further characterized in that said solvent is a saturated aliphatic hydrocarbon having from 6 to 8 carbon atoms, said molten phosphonitrilic chloride polymer is at a temperature of at least 120°C, said solvent vapor is passed through said molten phosphonitrilic chloride polymer at a rate of from about 0.02 to about 0.125 gram-mole per minute per gram-mole of phosphonitrilic chloride polymer and said trimeric and tetrameric cyclic phosphonitrilic chloride polymer are separated from the condensed solvent by crystallization.

* * * * *